United States Patent [19]

Tokuda et al.

[11] 4,331,685

[45] May 25, 1982

[54] CONTROL OF PLANT VIRUS DISEASES

[75] Inventors: Takuro Tokuda; Susumu Ikeda; Yoshikazu Kubota, all of Iwaki, Japan

[73] Assignee: Kureha Kagaku Kogyo Kabushiki Kaisha, Tokyo, Japan

[21] Appl. No.: 32,502

[22] Filed: Apr. 23, 1979

[30] Foreign Application Priority Data

May 12, 1978 [JP] Japan .................................. 53/56345

[51] Int. Cl.³ ...................... A01N 21/00; A01N 25/12
[52] U.S. Cl. ................................................... 424/325
[58] Field of Search .................... 424/325; 260/563 R

[56] References Cited

U.S. PATENT DOCUMENTS 2,383,564  8/1945  Ralston et al. ...................... 424/325
3,313,682  4/1967  Zenitz .................................. 424/325
3,655,888  4/1972  McManus et al. .................. 424/325
3,826,842  7/1974  Bordenca et al. ................... 424/325

FOREIGN PATENT DOCUMENTS 717519  9/1965  Canada ............................... 424/325
1165930  3/1964  Fed. Rep. of Germany ...... 424/325

*Primary Examiner*—Douglas W. Robinson
*Attorney, Agent, or Firm*—Wegner & Bretschneider

[57] ABSTRACT

Plants which have been sprayed with N-alkylalkanolamines and/or N-alkylalkanolammonium salts have been found to show much less tendency of suffering plant virus diseases when applied as they are or after being dissolved in solvent. The N-alkylalkanolamine is prepared by reacting an alkanolamine with an alkyl halide in the presence of a basic substance.

3 Claims, No Drawings

CONTROL OF PLANT VIRUS DISEASES

BACKGROUND OF THE INVENTION

In the control of plant virus diseases, it is the general practice to make use of passive measures such as a pulling-out of infected plants or control of virus-transmitting insects such as aphides, rice insects, leafhoppers, nematodes and the like. Since, however, these measures are not to control the virus diseases positively, there has been long desired a development of chemicals for effectively controlling the virus diseases. A number of substances which show some activity against plant-viral diseases are known including, for example, antimetabolites such as 2-thiouracil, 5-fluorouracil, 8-azaguanine and the like, antibiotics such as blasticidin S, formycin B, aabomycin A and the like, polysaccharides or proteins produced by microorganisms, and polysaccharides, proteins and tannins derived from plants. Of these, the antimetabolites or the antibiotics are disadvantageous in that they produce chemical injury on plants and show no long-lasting efficacy. On the other hand, the polysaccharides or proteins or tannins produced by microorganisms or derived from plant have a disadvantage that they can not block viral diseases from vectors such as aphides.

SUMMARY OF THE INVENTION

An object of the present invention is to provide a method for controlling plant-viral diseases by spraying a plant virus-controlling composition which comprises an effective amount of at least one compound selected from N-long chain alkylalkanolamines and their salts which cause no chemical injury against plant and is safe for man and animals and which are effective against a wide variety of viral diseases such as those of cucumber mosaic virus, tobacco mosaic virus and the like.

DETAILED DESCRIPTION OF THE INVENTION

The N-long chain alkylalkanolamine which is used, according to the invention, as an active component of the plant virus-controlling agent is prepared by bringing an alkyl halide to reaction with alkanolamine in the presence of a substance serving as a base.

The alkyl group of the N-long chain alkylalkanolamine is a saturated or unsaturated alkyl group containing 8–18 carbon atoms. The alkanolamine is one which contains, preferably, 2–6 carbon atoms and is, for example, ethanolamine, propanolamine, pentanolamine and hexanolamine including their various isomers. Above all, the linear chain alkanolamines are most preferable. The salts of the long chain alkylalkanolamines are salts of inorganic acids such as hydrochloric acid, hydrobromic acid, phosphoric acid, nitric acid, sulfuric acid and the like, and salts of organic acids such as acetic acid, propionic acid, malic acid, citric acid, maleic acid, fumaric acid, succinic acid, glycolic acid, tartaric acid, benzoic acid, hydroxybenzoic acid (ortho, meta and para), phthalic acid (ortho, meta and para), protocatechuic acid, gallic acid, caffeic acid, nicotinic acid, shikimic acid, chlorogenic acid, quinic acid, ascorbic acid, mandelic acid and the like.

Typical N-long chain alkylalkanolamines and their salts will be exemplified below.

| Compound No. | Structural Formula | Melting Point |
|---|---|---|
| (1) | $C_8H_{17}NHCH_2CH_2CH_2OH$ | 38°~40° C. |
| (2) | $C_8H_{17}NHCH_2CH(CH_3)-OH$ | 41°~43° C. |
| (3) | $C_8H_{17}NH-(CH_2)_4-OH$ | 38°~39° C. |
| (4) | $C_8H_{17}NH-(CH_2)_5-OH$ | 47°~49° C. |
| (5) | $C_8H_{17}NH-(CH_2)_6-OH$ | 64°~65° C. |
| (6) | $C_{10}H_{21}NH-CH_2CH_2CH_2OH$ | 43°~45° C. |
| (7) | $C_{10}H_{21}NH-CH_2CH(CH_3)-OH$ | 48°~50° C. |
| (8) | $C_{12}H_{25}NHCH_2CH_2OH$ | 45°~46° C. |
| (9) | $C_{12}H_{25}NHCH_2CH_2CH_2OH$ | 48°~50° C. |
| (10) | $C_{12}H_{25}NH-CH_2CHOH(CH_3)$ | 49°~51° C. |
| (11) | $C_{12}H_{25}NH-CH(CH_3)-CH_2OH$ | 55°~56° C. |
| (12) | $C_{12}H_{25}NH(CH_2)_4OH$ | 59°~61° C. |
| (13) | $C_{12}H_{25}NH(CH_2)_5OH$ | 60°~62° C. |
| (14) | $C_{12}H_{25}NH(CH_2)_6OH$ | 65°~67° C. |
| (15) | $C_{14}H_{29}NHCH_2CH_2CH_2OH$ | 57°~59° C. |
| (16) | $C_{14}H_{29}NHCH_2-CHOH(CH_3)$ | 64°~66° C. |
| (17) | $C_{16}H_{33}NHCH_2CH_2CH_2OH$ | 56°~58° C. |
| (18) | $C_{16}H_{33}NHCH_2CHOH(CH_3)$ | 66°~68° C. |
| (19) | $C_{18}H_{37}NHCH_2CH_2CH_2OH$ | 66°~68° C. |
| (20) | $C_{18}H_{37}NHCH_2CH(CH_3)-OH$ | 76°~78° C. |
| (21) | $C_{18}H_{37}NH(CH_2)_4OH$ | 68°~70° C. |
| (22) | $C_{18}H_{37}NH(CH_2)_5OH$ | 71°~73° C. |
| (23) | $C_8H_{17}\overset{\oplus}{N}H_2-(CH_2)_5OH$ · $HO-C_6H_4-COO^{\ominus}$ | 120°~121° C. |
| (24) | $C_8H_{17}\overset{\oplus}{N}H_2-(CH_2)_5OH$ · $(HO)_2-C_6H_3-COO^{\ominus}$ | 105°~106° C. |
| (25) | $C_8H_{17}\overset{\oplus}{N}H_2-(CH_2)_5OH$ · $(HO)_3-C_6H_2-COO^{\ominus}$ | 54°~56° C. |
| (26) | $C_{12}H_{25}\overset{\oplus}{N}H_2-(CH_2)_3OH$ · $Cl^{\ominus}$ | 161°~163° C. |
| (27) | $C_{12}H_{25}\overset{\oplus}{N}H_2-(CH_2)_3OH$ · $C_6H_5-COO^{\ominus}$ | (oily) |
| (28) | $C_{12}H_{25}\overset{\oplus}{N}H_2-(CH_2)_3OH$ · $(HO)_3-C_6H_2-COO^{\ominus}$ | 110°~111° C. |
| (29) | $C_{12}H_{25}\overset{\oplus}{N}H_2-(CH_2)_3OH$ · nicotinate | (oily) |

| Compound No. | Structural Formula | Melting Point |
|---|---|---|
| (30) | $[C_{12}H_{25}\overset{\oplus}{N}H_2-(CH_2)_3OH]_2$<br>$CH_2COO^{\ominus}$<br>$HO-CH-COO^{\ominus}$ | 84°–86° C. |
| (31) | $[C_{12}H_{25}\overset{\oplus}{N}H_2-(CH_2)_3OH]_2$<br>$CH_2-COO^{\ominus}$<br>$CH_2-COO^{\ominus}$ | 65°–67° C. |
| (32) | $C_{12}H_{25}\overset{\oplus}{N}H_2-(CH_2)_3OH$<br>$COO^{\ominus}$<br>$CH_2OH$ | 81°–83° C. |
| (33) | $[C_{12}H_{25}\overset{\oplus}{N}H_2-(CH_2)_3OH]_3$<br>$CH_2-COO^{\ominus}$<br>$HO-C-COO^{\ominus}$<br>$CH_2-COO^{\ominus}$ | 104°–106° C. |
| (34) | $C_{12}H_{25}\overset{\oplus}{N}H_2-(CH_2)_3OH$<br>$HO-\langle\bigcirc\rangle-COO^{\ominus}$ | 152°–154° C. |
| (35) | $C_{12}H_{25}\overset{\oplus}{N}H_2-(CH_2)_3OH$<br>$\langle\bigcirc\rangle-CH=CH-COO^{\ominus}$<br>$OH$ | 64°–66° C. |
| (36) | $C_{12}H_{25}\overset{\oplus}{N}H_2-(CH_2)_3OH$<br>$HO-\langle\bigcirc\rangle-CH=CH-COO^{\ominus}$ | 80°–82° C. |
| (37) | $C_{12}H_{25}\overset{\oplus}{N}H_2-(CH_2)_3OH$<br>$HO$<br>$HO-\langle\bigcirc\rangle-CH=CH-COO^{\ominus}$ | 79°–81° C. |
| (38) | $C_{12}H_{25}\overset{\oplus}{N}H_2-(CH_2)_3OH$<br>$HO$<br>$HO-\langle\bigcirc\rangle-COO^{\ominus}$ | 133°–135° C. |
| (39) | $C_{12}H_{25}\overset{\oplus}{N}H_2-(CH_2)_3OH$<br>$\langle\bigcirc\rangle-COO^{\ominus}$<br>$HO$ | 60°–62° C. |
| (40) | $C_{12}H_{25}\overset{\oplus}{N}H_2-(CH_2)_3OH$<br>$\langle\bigcirc\rangle-COO^{\ominus}$<br>$OH$ | (oily) |
| (41) | $C_{12}H_{25}\overset{\oplus}{N}H_2-(CH_2)_3OH$<br>$\overset{O}{\underset{OCCH=CH}{\parallel}}-\langle\bigcirc\rangle-OH$<br>$^{\ominus}OOC-\langle\bigcirc\rangle-OH$<br>$HO\quad OH$ | 73°–75° C. |
| (42) | $C_{12}H_{25}\overset{\oplus}{N}H_2-(CH_2)_3OH$<br>$HO$<br>$\langle\bigcirc\rangle-CH=CH-COO^{\ominus}$ | 102°–103° C. |
| (43) | $C_{12}H_{25}\overset{\oplus}{N}H_2-(CH_2)_5-OH$<br>$HO-\langle\bigcirc\rangle-COO^{\ominus}$ | 132°–133° C. |
| (44) | $C_{12}H_{25}\overset{\oplus}{N}H_2-(CH_2)_5OH$<br>$HO$<br>$HO-\langle\bigcirc\rangle-COO^{\ominus}$ | 123°–124° C. |
| (45) | $C_{12}H_{25}\overset{\oplus}{N}H_2-(CH_2)_5OH$<br>$HO$<br>$HO-\langle\bigcirc\rangle-COO^{\ominus}$<br>$HO$ | 66°–68° C. |
| (46) | $C_{12}H_{25}\overset{\oplus}{N}H_2-(CH_2)_6OH$<br>$OH$<br>$\langle\bigcirc\rangle-CH-COO^{\ominus}$ | 114°–115° C. |
| (47) | $C_{18}H_{37}\overset{\oplus}{N}H_2-(CH_2)_3OH$<br>$HO$<br>$HO-\langle\bigcirc\rangle-COO^{\ominus}$<br>$HO$ | 66°–68° C. |
| (48) | $[C_{18}H_{37}\overset{\oplus}{N}H_2-(CH_2)_3OH]_2$<br>$CH_2-COO^{\ominus}$<br>$CH_2-COO^{\ominus}$ | 82°–84° C. |
| (49) | $[C_{18}H_{37}\overset{\oplus}{N}H_2-(CH_2)_3OH]_2$<br>$CH_2-COO^{\ominus}$<br>$HO-CH-COO^{\ominus}$ | 88°–90° C. |
| (50) | $C_{18}H_{37}\overset{\oplus}{N}H_2-(CH_2)_3OH$<br>$HO-\langle\bigcirc\rangle-COO^{\ominus}$ | 150°–152° C. |
| (51) | $C_{18}H_{37}\overset{\oplus}{N}H_2-(CH_2)_3OH$<br>$\langle\bigcirc\rangle-CH=CH-COO^{\ominus}$<br>$OH$ | 79°–80° C. |
| (52) | $C_{18}H_{37}\overset{\oplus}{N}H_2-(CH_2)_3OH$<br>$HO-\langle\bigcirc\rangle-CH=CH-COO^{\ominus}$ | 99°–100° C. |
| (53) | $C_{18}H_{37}\overset{\oplus}{N}H_2-(CH_2)_3OH$<br>$HO$<br>$HO-\langle\bigcirc\rangle-CH=CH-COO^{\ominus}$ | 90°–91° C. |
| (54) | $C_{18}H_{37}\overset{\oplus}{N}H_2(CH_2)_3OH$<br>$HO$<br>$HO-\langle\bigcirc\rangle-COO^{\ominus}$ | 134°–136° C. |
| (55) | $C_{18}H_{37}\overset{\oplus}{N}H_2(CH_2)_3OH$<br>$HO$<br>$HO-\langle\bigcirc\rangle-COO^{\ominus}$<br>$HO$ | 58°–60° C. |

-continued

| Compound No. | Structural Formula | Melting Point |
|---|---|---|
| (56) | $C_{18}H_{37}\overset{\oplus}{N}H_2(CH_2)_3OH$ <br> 3-hydroxybenzoate anion (HO-C$_6$H$_4$-COO$^\ominus$) | 85°~87° C. |
| (57) | $C_{18}H_{37}\overset{\oplus}{N}H_2(CH_2)_3OH$ <br> ascorbate-type anion (CH$_2$OH group, furanone with $^\ominus$O and OH, =O) | 65°~67° C. |
| (58) | $C_{18}H_{37}\overset{\oplus}{N}H_2(CH_2)_3OH$ <br> salicylate anion (2-hydroxybenzoate, OH ortho to COO$^\ominus$) | 60°~61° C. |
| (59) | $C_{18}H_{37}\overset{\oplus}{N}H_2(CH_2)_3OH$ <br> chlorogenate-type anion ($^\ominus$OOC-cyclohexane(HO,OH,OH)-O-C(=O)-CH=CH-C$_6$H$_3$(OH)(OH)) | 105°~107° C. |
| (60) | $C_{18}H_{37}\overset{\oplus}{N}H_2(CH_2)_3OH$ <br> p-hydroxycinnamate anion (HO-C$_6$H$_4$-CH=CH-COO$^\ominus$) | 119°~120° C. |
| (61) | $C_{18}H_{37}\overset{\oplus}{N}H_2(CH_2)_5OH$ <br> p-hydroxybenzoate anion (HO-C$_6$H$_4$-COO$^\ominus$) | 105°~107° C. |
| (62) | $C_{18}H_{37}\overset{\oplus}{N}H_2(CH_2)_5OH$ <br> 3,4-dihydroxybenzoate anion (HO, HO-C$_6$H$_3$-COO$^\ominus$) | 114°~116° C. |
| (63) | $C_{18}H_{37}\overset{\oplus}{N}H_2(CH_2)_5OH$ <br> 3,4,5-trihydroxybenzoate (gallate) anion (HO, HO, HO-C$_6$H$_2$-COO$^\ominus$) | 83°~85° C. |

The preparation of the compounds useful in the invention will be particularly illustrated in the following Synthetic Examples.

SYNTHETIC EXAMPLE 1 (Synthesis of Compound No. (9))

20.5 g (0.1 mole) of lauryl chloride and 8.3 g (0.11 moles) of 3-aminopropanol-1 were dissolved in 150 ml of n-propanol, to which was added 10 g of sodium carbonate, followed by heating and refluxing for 24 hours. After completion of the reaction, the solvent was distilled off and the residue was dissolved in chloroform, washed with a saturated salt solution and dried with anhydrous sodium sulfate, followed by distilling off and recrystallizing from n-hexane to obtain 19.5 g of colorless needle-like crystals with a melting point of 48°-50° C.

| Elementary Analysis: | C (%) | H (%) | N (%) |
|---|---|---|---|
| Calculated for C$_{15}$H$_{33}$NO | 74.01 | 13.66 | 5.75 |
| Found | 73.6 | 13.4 | 5.8 |

SYNTHETIC EXAMPLE 2 (Synthesis of Compound (34))

2.43 g (0.01 mole) of N-lauryl-3-aminopropanol-1 (Compound No. (9)) was dissolved in 30 ml of acetone, which was then poured into a solution of 1.38 g (0.01 mole) of p-hydroxybenzoic acid in 30 ml of acetone, whereupon crystals immediately precipitated. The crystals were filtered and well washed with cold acetone to obtain 3.7 g of colorless needle-like crystals.

| Elementary Analysis: | C (%) | H (%) | N (%) |
|---|---|---|---|
| Calculated for C$_{22}$H$_{39}$NO$_4$ | 69.25 | 10.30 | 3.67 |
| Found | 69.2 | 10.1 | 3.6 |

In practical application, the above compounds may be used without addition of any other components or may be admixed with a suitable carrier, diluent, spreader or other additive to prepare a wettable powder, dust, emulsion, granular or oil similarly to the case of ordinary agricultural chemicals. Further, the compounds may be used in combination with other agricultural chemicals, fertilizers and the like.

The present invention will be particularly illustrated by the following examples and experimental examples, in which kinds of additives and their mixing ratios to the compounds used in the invention are specified but any other additives and a wide range of the mixing ratio may be used without departing from the scope of the invention. In the examples, parts are by weight unless otherwise indicated.

EXAMPLE 1 (Wettable powder)

| | |
|---|---|
| N-laurylpropanolamine gallate (Compound No. (28)) | 20 parts |
| Polyethylenealkyl phenyl ether emulsion | 2 parts |
| Diatomaceous earth | 78 parts |

The composition of the above formulation which was mixed and milled was suspended in water and sprayed.

EXAMPLE 2 (Dust)

| | |
|---|---|
| N-laurylpentanolamine (Compound No. (13)) | 5 parts |
| Clay | 95 parts |

The composition of the above formulation was uniformly mixed and milled, and then sprayed.

EXPERIMENTAL EXAMPLE 1

An activity of inhibiting formation of local viral symptoms against a tobacco mosaic virus (TMV) (hereinlater referred to merely as inhibiting activity) was determined by a half-leaf method using primary leaves of a kidney bean (variety: Otebo). The primary leaves of the bean were inoculated with TMV. Immediately after the inoculation, the half of each leaf was applied with a test liquid and the other half were applied with water by the use of swabs. Each tested liquid had a concentration of 500 ppm and the concentration of TMV was controlled so that about 50 local viral symptoms per half leaf were formed in the water-applied plots.

Ten half leaves were tested for one chemical and the inhibiting rate was calculated from the following equation:

Inhibiting rate (%) =
$$\left(1 - \frac{\text{The total number of viral symptoms in the chemical-treated plot}}{\text{The total number of viral symptoms in water-treated plot}}\right) \times 100$$

The inhibiting rate was assessed as follows:

| Inhibiting Rate (%) | Assessment |
|---|---|
| 100–90 | A |
| 90–70 | B |
| 70–50 | C |
| 50–30 | D |
| below 30 | E |

The test results are shown in Table 1 below, in which the compounds tested are indicated merely by the compound numbers exemplified hereinbefore.

Table 1

| Compound | Assessment | Compound | Assessment | Compound | Assessment |
|---|---|---|---|---|---|
| (1) | B | (23) | A | (45) | A |
| (2) | C | (24) | A | (46) | B |
| (3) | C | (25) | A | (47) | A |
| (4) | B | (26) | A | (48) | B |
| (5) | B | (27) | A | (49) | B |
| (6) | A | (28) | A | (50) | A |
| (7) | C | (29) | A | (51) | A |
| (8) | A | (30) | A | (52) | A |
| (9) | A | (31) | A | (53) | A |
| (10) | B | (32) | A | (54) | A |
| (11) | C | (33) | A | (55) | A |
| (12) | B | (34) | A | (56) | A |
| (13) | A | (35) | A | (57) | A |
| (14) | B | (36) | A | (58) | A |
| (15) | A | (37) | A | (59) | A |
| (16) | B | (38) | A | (60) | A |
| (17) | A | (39) | A | (61) | A |
| (18) | C | (40) | A | (62) | A |
| (19) | A | (41) | A | (63) | A |
| (20) | B | (42) | A | Water | E |
| (21) | B | (43) | A | | |
| (22) | A | (44) | A | | |

EXPERIMENTAL EXAMPLE 2

The compounds which had been evaluated as "A" in Experimental Example 1 were further tested to determine their antiviral activity on cucumber mosaic virus (CMV) by a test in which ten tobacco seedlings (variety: KY-57) that had been grown for 2 months after seeding were used to one compound to be tested. There was used as an inoculum of the virus a 1:100 dilution of a pressed juice from infested leaves of the tobacco by the virus for the CMV, which was smeared on and inoculated in developed leaves of one tobacco seedling. Immediately after the inoculation, a test liquid having a concentration of 500 ppm was sprayed over the leaves in an amount of 10 ml/seedling. In reference plots, water was sprayed.

Ten days after the inoculation of the CMV, the inhibiting rate was checked and indicated by $$\frac{\text{The number of non-infected seedlings}}{\text{The number of tested seedlings}}$$

The inhibiting efficacy was evaluated as follows:

| The number of non-infected seedlings / The number of tested seedlings | Evaluation |
|---|---|
| 10/10–8/10 | A |
| 7/10–5/10 | B |
| 4/10–2/10 | C |
| below 1/10 | D |

The test results are shown in Table 2 below.

Table 1

| Compound No. | Evaluation | Chemical Injury | Compound No. | Evaluation | Chemical injury |
|---|---|---|---|---|---|
| (6) | B | no | (39) | A | no |
| (8) | B | Inhibition of growth | (40) | A | no |
| (9) | A | Inhibition of growth | (41) | B | no |
| (13) | A | no | (42) | B | no |
| (15) | B | Inhibition of growth | (43) | A | no |
| (17) | A | no | (44) | A | no |
| (19) | A | no | (45) | A | no |
| (22) | B | no | (47) | B | no |
| (23) | A | no | (50) | A | no |
| (24) | B | no | (51) | B | no |
| (25) | B | no | (52) | B | no |
| (26) | A | Inhibition of growth | (53) | A | no |
| (27) | A | no | (54) | B | no |
| (28) | A | no | (55) | B | no |
| (29) | A | no | (56) | B | no |
| (30) | B | no | (57) | A | no |
| (31) | B | no | (58) | B | no |
| (32) | A | no | (59) | B | no |
| (33) | A | no | (60) | B | no |
| (34) | A | no | (61) | B | no |
| (35) | A | no | (62) | B | no |
| (36) | B | no | (63) | B | no |
| (37) | A | no | Water | D | no |
| (38) | A | no | | | |

EXPERIMENTAL EXAMPLE 3

The compounds which had been evaluated as "A" in Experimental Example 2 were still further tested. Cucumber seedlings (variety: Chikanarisanto) which had been grown for 2 weeks after seeding was sprayed with a test liquid with a concentration of 500 ppm and air-dried for about 3 hours. After the air-drying, non-alar green peach aphides which had sucked a juice of infested cucumber with CMV were transmigrated on the liquid-sprayed cucumber seedlings at a rate of 5 aphides/seedling. In the day after the liquid treatment, an insecticide (DDVP) was sprayed to expel the green peach aphides. One week after the liquid treatment, the antiviral activity of each chemical was checked to indicate the number of non-infected seedling/the number of tested seedlings.

The results are shown in Table 3 below.

Table 3

| Compound No. | The number of non-infected seedlings/the number of tested seedlings | Chemical injury | Compound No. | The number of non-infected seedlings/the number of tested seedlings | Chemical injury |
| --- | --- | --- | --- | --- | --- |
| (9) | 8/10 | Inhibition of growth | (35) | 6/10 | no |
| (13) | 6/10 | no | (37) | 8/10 | no |
| (17) | 6/10 | no | (38) | 5/10 | no |
| (19) | 7/10 | no | (39) | 6/10 | no |
| (23) | 7/10 | no | (40) | 8/10 | no |
| (26) | 7/10 | Inhibition of growth | (43) | 8/10 | no |
| (27) | 7/10 | no | (44) | 6/10 | no |
| (28) | 8/10 | no | (45) | 6/10 | no |
| (29) | 6/10 | no | (50) | 7/10 | no |
| (32) | 5/10 | no | (53) | 7/10 | no |
| (33) | 6/10 | no | (57) | 6/10 | no |
| (34) | 8/10 | no | Water | 0/10 | no |

Accordingly, the preferred compounds of the invention can be summarized as follows:

(I) A group of the N-long chain alkylalkanolamines having the formula of $$R_1-NH-R_2-OH$$

in which $R_1$ is a saturated alkyl of $C_8-C_{18}$, preferably, straight chain alkyl of $C_{11}-C_{17}$, and $R_2$ is a saturated alkylidene of $C_2-C_6$, preferably, straight chain alkylidene of $C_3-C_5$.

(II) A group of aromatic acid salts of the compounds of group (I).

What is claimed is:

1. A method for combatting and preventing viral diseases in plants belonging to the monocotyledenous and dicotyledenous angiosperms which comprise administering to said plants a composition comprising an antivirally effective amount of at least one N-higher alkylalkanolamine of the formula:

$$R^1-NH-R^2-OH$$

wherein
$R^1$ is an alkyl group having 8 to 18 carbon atoms and
$R^2$ is an alkylene group having 2 to 6 carbon atoms, or one of the salts thereof.

2. A method as claimed in claim 1, wherein the N-higher alkylalkanolamine has the formula:

$$CH_3.(CH_2)_m.NH(CH_2)_n.OH$$

wherein
m is a integer of 11 to 17 and
n is an integer of 3 to 5.

3. A method as claimed in claim 1 or 2, wherein the N-higher alkylalkanolamine is a compound selected from the group consisting of N-dodecyl pentanolamine, N-hexadecyl propanolamine and N-octadecyl propanolamine.

* * * * *